(12) United States Patent
Sreedharala et al.

(10) Patent No.: US 12,064,414 B2
(45) Date of Patent: Aug. 20, 2024

(54) STABLE AMORPHOUS ELIGLUSTAT PREMIX AND PROCESS FOR THE PREPARATION THEREOF

(71) Applicant: AIZANT DRUG RESEARCH SOLUTIONS PRIVATE LIMITED., Hyderabad (IN)

(72) Inventors: Venkata Nookaraju Sreedharala, Hyderabad (IN); Vijaya Rajesh Kumar Yelchuri, Hyderabad (IN)

(73) Assignee: AIZANT DRUG RESEARCH SOLUTIONS PRIVATE LIMITED., Hyderabad (IN)

( * ) Notice: Subject to any disclaimer, the term of this patent is extended or adjusted under 35 U.S.C. 154(b) by 0 days.

(21) Appl. No.: 16/956,269

(22) PCT Filed: Dec. 4, 2018

(86) PCT No.: PCT/IN2018/050812
§ 371 (c)(1),
(2) Date: Jun. 19, 2020

(87) PCT Pub. No.: WO2019/123476
PCT Pub. Date: Jun. 27, 2019

(65) Prior Publication Data
US 2020/0316025 A1    Oct. 8, 2020

(30) Foreign Application Priority Data
Dec. 20, 2017    (IN) .............................. 201741045763

(51) Int. Cl.
| | | |
|---|---|---|
| *A61K 9/00* | (2006.01) | |
| *A61K 9/20* | (2006.01) | |
| *A61K 31/4025* | (2006.01) | |
| *A61K 45/06* | (2006.01) | |

(52) U.S. Cl.
CPC .......... *A61K 31/4025* (2013.01); *A61K 9/006* (2013.01); *A61K 9/20* (2013.01)

(58) Field of Classification Search
CPC ........ A61K 9/006; A61K 9/0056; A61K 9/20; A61K 9/2018; A61K 9/2031; A61K 9/2054; A61K 9/7007; A61K 47/26; A61K 2300/00; A61K 9/10; A61K 9/14; A61K 47/36; A61K 9/2095; A61K 9/2077; A61K 45/06; A61K 9/0053; A61K 9/19; A61P 3/00; A61P 13/12; A61P 1/16; A61P 35/04; A61P 43/00
See application file for complete search history.

(56) References Cited

U.S. PATENT DOCUMENTS

| | | |
|---|---|---|
| 6,855,830 B2 | 2/2005 | Hirth et al. |
| 7,196,205 B2 | 3/2007 | Siegel et al. |
| 7,265,228 B2 | 9/2007 | Hirth et al. |
| 7,615,573 B2 | 11/2009 | Siegel et al. |
| 7,763,738 B2 | 7/2010 | Hirth et al. |
| 8,138,353 B2 | 3/2012 | Hirth et al. |
| 2003/0031720 A1* | 2/2003 | Laich ................... A61K 9/1623 264/5 |
| 2012/0296088 A1 | 11/2012 | Hirth et al. |
| 2013/0137743 A1 | 5/2013 | Liu et al. |
| 2017/0334916 A1* | 11/2017 | Skerlj .................... A61P 25/18 |

FOREIGN PATENT DOCUMENTS

| | | |
|---|---|---|
| IN | 201621009771 | 11/2017 |
| WO | 2011/066352 A1 | 6/2011 |
| WO | 2016/001885 A2 | 1/2016 |

OTHER PUBLICATIONS

Aulton. Powder flow. Aug. 2, 2015. <https://clinicalgate.com/powder-flow/>. (Year: 2015).*
Tsutomu Konno, "Physical and Chemical Changes of Medicinals in Mixtures with Absorbents in Solid State. IV, Study on Reduced-Pressure Mixing for Practical Use of Amorphous Mixture of Flufenamic Acid," Chem. Pharm .Bull. 38(7) 2003-2007, Jul. 1990.
International Search Report for Serial No. PCT/IN2018/050812 dated Jun. 3, 2019.
Written Opinion for Serial No. PCT/IN2018/050812 dated Jun. 3, 2019.

* cited by examiner

*Primary Examiner* — Tracy Liu
(74) *Attorney, Agent, or Firm* — Pergament & Cepeda LLP; Milagros A. Cepeda; Edward D. Pergament

(57) ABSTRACT

The present invention relates to pharmaceutical compositions of Eliglustat. In particular the present invention relates to stable amorphous Eliglustat premix having enhanced stability and dissolution properties. The present invention also provide a stable premix composition comprising amorphous Eliglustat or a pharmaceutical acceptable salt thereof, pharmaceutical compositions comprising the premixes, and processes for preparing the same. The compositions prepared in the present invention includes sublingual or mouth dissolving tablets, and capsules of Eliglustat and/or its pharmaceutically acceptable salts thereof and at least one pharmaceutically acceptable carrier.

12 Claims, 4 Drawing Sheets

STABLE AMORPHOUS ELIGLUSTAT PREMIX AND PROCESS FOR THE PREPARATION THEREOF

CROSS-REFERENCE TO RELATED APPLICATIONS

This application is a National Stage application of International Patent Application No. PCT/IN2018/050812, filed on Dec. 4, 2018, which claims priority to Indian Patent Application No. 201741045763 filed on Dec. 20, 2017, each of which is hereby incorporated by reference in its entirety.

TECHNICAL FIELD

The present invention relates to pharmaceutical compositions of Eliglustat. In particular the present invention relates to stable amorphous Eliglustat premix, method of preparation of the same and pharmaceutical compositions comprising the said premix.

BACKGROUND

Chemically Eliglustat is named N-[(1R,2R)-2-(2,3-dihydro-1,4-benzodioxin-6-yl)-2-hydroxy-1-(1-pyrrolidinyl-methyl)ethyl]-Octanamide(2R,3R)-2,3-dihydroxybutane-dioate and the hemitartrate salt of Eliglustat has the structural formula as shown in Formula I.

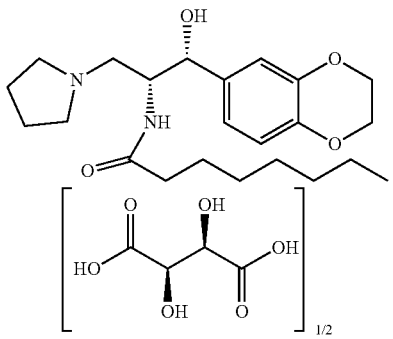

Eliglustat hemitartrate (Genz-112638), currently approved by US FDA & EU MoH for Genzyme, is a glucocerebroside (glucosylceramide) synthase inhibitor for the treatment of Gaucher disease and other lysosomal storage disorders. Eliglustat hemitartrate is orally active with potent effects on the primary identified molecular target for type 1 Gaucher disease and other glycosphingolipidoses, appears likely to fulfill high expectations for clinical efficacy. Gaucher disease belongs to the class of lysosomal diseases known as glycosphingolipidoses, which result directly or indirectly from the accumulation of glycosphingolipids, many hundreds of which are derived from glucocerebroside. The first step in glycosphingolipid biosynthesis is the formation of glucocerebroside, the primary storage molecule in Gaucher disease, via glucocerebroside synthase (uridine diphosphate [UDP]-glucosylceramide glucosyl transferase). Eliglustat hemitartrate is based on improved inhibitors of glucocerebroside synthase.

U.S. Pat. No. 7,196,205 discloses a process for the preparation of Eliglustat or a pharmaceutically acceptable salt thereof.

U.S. Pat. Nos. 6,855,830, 7,265,228, 7,615,573, 7,763,738, 8,138,353, U.S. patent application publication No. 2012/296088 discloses process for preparation of Eliglustat and intermediates thereof.

U.S. patent application publication No. 2013/137743 discloses (i) a hemitartrate salt of Eliglustat, (ii) a hemitartrate salt of Eliglustat, wherein at least 70% by weight of the salt is crystalline, (iii) a hemitartrate salt of Eliglustat, wherein at least 99% by weight of the salt is in a single crystalline form.

It has been disclosed earlier that the amorphous forms in a number of drugs exhibit different dissolution characteristics and in some cases different bioavailability patterns compared to crystalline forms [Konne T, *Chem pharm Bull.*, 38, 2003(1990)]. For some therapeutic indications one bioavailability pattern may be favored over another. An amorphous form of Cefuroxime axetil is a good example for exhibiting higher bioavailability than the crystalline form.

Solid amorphous dispersions of drugs are known generally to improve the stability and solubility of drug products. However, such dispersions are generally unstable over time. Amorphous dispersions of drugs tend to convert to crystalline forms over time, which can lead to improper dosing due to differences of the solubility of crystalline drug material compared to amorphous drug material.

There remains a need to provide solid state forms of Eliglustat hemitartrate which are advantageous in a cost effective and environment friendly manner.

Though amorphous Eliglustat hemitartrate and its process of manufacture has been described in Patent Application WO 2016/001885 A3, Eliglustat hemitartrate in premix form, is a novel approach by the present inventors towards attaining a significantly more stable amorphous product having better dissolution properties that can be easily formulated to give pharmaceutical compositions.

U.S. patent application publication No. 2013/137743 also discloses a salt between Eliglustat and hydrochloric acid or tartaric acid that is described to be "hygroscopic and non-crystalline and therefore unacceptable for use in a pharmaceutical product". The present disclosure provides amorphous Eliglustat premix that have advantageous properties over other solid state forms of Eliglustat and over the hygroscopic and non-crystalline Eliglustat salts of prior art, as the prior art amorphous forms are very unstable and deliquescent which is totally undesirable for pharmaceutical preparations. Thus the inventors of the present invention found that the Eliglustat hemitartrate premixes prepared using the present approach is stable and non-deliquescent, so desirable and better for preparation of solid dosage forms.

Premixes are characterized by a variety of associated properties such as stability, flow, and solubility. Typical premixes represent a compromise of the above properties, as for example, an increase in stability and dissolution properties of the premix. Although there are a variety of premixes, there is a continual search in this field of art for premixes that exhibit an improved mix of properties. The present inventors have found a novel and inventive amorphous Eliglustat premix which is stable even under stress conditions. Thus, the instant invention provides a premix in which Eliglustat hemitartrate exists in stable amorphous form and process of manufacture of the premix and pharmaceutical compositions comprising said Eliglustat hemitartrate premix.

SUMMARY

An object of the present invention is to provide stable amorphous Eliglustat hemitartrate premix having enhanced stability and dissolution properties.

Another object of the present invention is to provide simple, cost-effective and environment friendly method for preparation of said stable amorphous Eliglustat hemitartrate premix using Eliglustat as the input material.

Yet another object of the invention is to provide pharmaceutical compositions comprising said stable amorphous Eliglustat premix.

Another object of the present invention is to provide a stable premix composition comprising amorphous Eliglustat or a pharmaceutical acceptable salt thereof, pharmaceutical compositions comprising the premixes, and processes for preparing the same.

A further object of the present invention is to provide sublingual or mouth dissolving tablets of Eliglustat and/or its pharmaceutically acceptable salts thereof and at least one pharmaceutically acceptable carrier.

DETAILED DESCRIPTION

Figure 1:
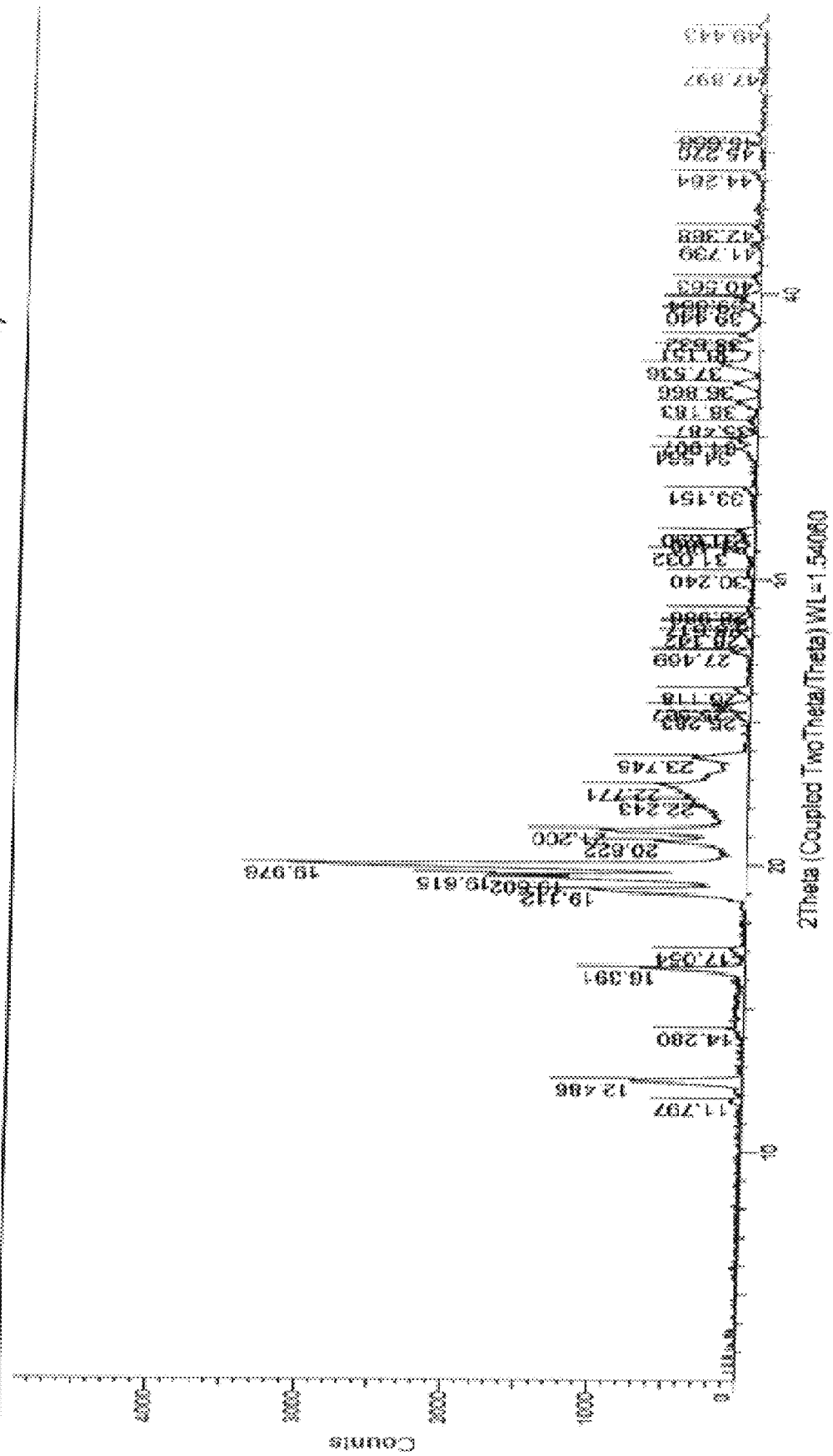
FIG. 1: PXRD pattern of Eliglustat Tartrate Capsule.

In one embodiment the present invention provides stable amorphous Eliglustat premix having enhanced and better stability and dissolution properties.

The term "premix" is used herein to describe combinations of Eliglustat hemitartrate and at least one pharmaceutically acceptable excipient, wherein individual particles of the components cannot be distinguished using techniques such as optical microscopy. In embodiments, the drug is considered as being uniformly or non-uniformly distributed over surfaces of excipient particles. In other embodiments, the premixes are considered to be in the nature of molecular dispersions, or solid solutions. Simple mixtures of powdered ingredients will not constitute premixes.

The term "stable" as used herein refers to physical stability and/or chemical stability of the active agent in the composition, wherein changes in the drug assay values and/or impurities content are less than about 10%, during stability study storage of the composition at 25° C. and 60% relative humidity (RH), or 30° C. and 65% RH, or 40° C. and 75% RH, for durations such as 3, 6, 12, 18, or 24 months.

In another preferred embodiment of the invention, the present invention provides a stable Eliglustat premix having enhanced flow property, stability, dissolution properties that can be easily formulated into pharmaceutical compositions.

In another embodiment of the invention, the present invention provides a stable amorphous Eliglustat premix comprising Eliglustat and at least one pharmaceutically acceptable excipient.

The term "excipient" or "pharmaceutically acceptable excipient" means a component of a pharmaceutical product that is not an active ingredient, and includes but not limited to filler, diluent, disintegrants, glidants, stabilizers, surface active agents etc. The excipients that are useful in preparing a pharmaceutical composition are generally safe, non-toxic and neither biologically nor otherwise undesirable, and are acceptable for veterinary use as well as human pharmaceutical use. One excipient can perform more than one function.

The "Pharmaceutically acceptable excipient" as used in the specification includes both one and more than one such excipient.

Any of the pharmaceutically acceptable excipient described in the specification can be used in the process of preparing stable amorphous Eliglustat premix.

The pharmaceutically acceptable excipients used in the process of preparing stable amorphous Eliglustat premix may also be termed as "premixing agents".

The suitable premixing agent or pharmaceutically acceptable excipient(s) discussed in the specification includes but not limited to diluents, lubricants, disintegrants, glidants, stabilizers & surface active agents or mixtures thereof. Preferably the premixing agents or pharmaceutically acceptable excipients used in the process of preparing stable amorphous Eliglustat premix can be selected from the group consisting of polyvinylpyrrolidone (also called povidone), copovidone, polyvinyl alcohol, polyethylene glycol, polyol (Lactose, Mannitol), sodium starch glycolate, colloidal silicon dioxide (aerosil), hydroxypropyl cellulose, hydroxypropyl methylcellulose, methyl cellulose, carboxymethyl cellulose, sodium carboxymethyl cellulose, hydroxyethylcellulose, polyvinyl acetate, cyclodextrins, gelatins, hypromellose phthalate, sugars, silicates such as magnesium aluminometasilicate and combinations comprising one or more of the foregoing agents, Preferably selected from copovidone, lactose, magnesium aluminometasilicate, polyethylene glycol (PEG) and aerosol 200.

In another embodiment, the invention provides a process for preparation of stable amorphous Eliglustat premix comprising the steps of:
(i) providing a solution of Eliglustat in a solvent;
(ii) adding suitable premixing agent(s); and
(iii) substantially removing the solvents from the solution to afford stable amorphous Eliglustat premix.

The term "substantially removing" the solvent refers to at least 80%, specifically greater than about 85%, more specifically greater than about 90%, still more specifically greater than about 99%, and most specifically essentially complete (100%), removal of the solvent from the solvent solution.

The solvent employed in step (i) is selected from halogenated hydrocarbons such as dichloromethane, 1,2-dichloroethane, chloroform and carbon tetrachloride; alcohols such as methanol, ethanol, isopropyl alcohol, 1-propanol, 2-propanol, 1-butanol, 2-butanol, and t-butyl alcohol; ketones such as acetone, ethyl methyl ketone, diethyl ketone, and methyl isobutyl ketone; esters such as ethyl acetate, n-propyl acetate, n-butyl acetate and t-butyl acetate; ethers such as diethyl ether, dimethyl ether, diisopropyl ether, methyl t-butyl ether and 1,4-dioxane; nitriles such as acetonitrile and propionitrile; water and mixtures thereof.

The Eliglustat used in step (i) is selected from crystalline form (s) or amorphous forms of Eliglustat free base or pharmaceutically acceptable salts thereof.

Removal of solvent in step (iii) is accomplished, for example, by substantially complete evaporation of the solvent, concentrating the solution or distillation of solvent, under inert atmosphere to obtain the stable amorphous Eliglustat hemitartrate premix.

In another embodiment, the solvent is removed by evaporation. Evaporation can be achieved at sub-zero temperatures by lyophilisation or freeze-drying techniques. The solution may also be completely evaporated in, for example, a pilot plant Rota vapor, a Vacuum Paddle Dryer or in a conventional reactor under vacuum above at about 720 mm Hg by flash evaporation techniques by using an agitated thin film dryer ("ATFD"), or evaporated by spray drying to obtain a dry amorphous powder.

The distillation process can be performed at atmospheric pressure or at reduced pressure. Specifically, the solvent is removed at a pressure of about 760 mm Hg or less, more specifically at about 400 mm Hg or less, still more specifically at about 80 mm Hg or less, and most specifically from about 30 to about 80 mm Hg.

Solvents can also be removed by spray-drying, in which a solution comprising Eliglustat and a premixing agent is sprayed into the spray drier at the flow rate ranging from 10 to 300 ml/hr, specifically 40 to 200 ml/hr. The air inlet temperature to the spray drier used may range from about 30° C. to about 15° C., specifically from about 65° C. to about 110° C. and the outlet air temperature used may range from about 30° C. to about 90° C.

Another suitable method is vertical agitated thin-film drying (or evaporation). Agitated thin film evaporation technology involves separating the volatile component using indirect heat transfer coupled with mechanical agitation of the flowing film under controlled conditions. In vertical agitated thin-film drying (or evaporation) (ATFD-V), the starting solution is fed from the top into a cylindrical space between a centered rotary agitator and an outside heating jacket. The rotor rotation agitates the downside-flowing solution while the heating jacket heats it.

The Eliglustat with the premixing agent obtained by process disclosed herein may be further dried, preferably spin dried, in, for example, a Vacuum Tray Dryer, a Rotocon Vacuum Dryer, a Vacuum Paddle Dryer or a pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In yet another preferred embodiment, the present invention provides a simple, economical and easy process for manufacturing the presently disclosed Amorphous Eliglustat premix comprising:
   a. dissolving a mixture of Eliglustat and tartaric acid in an organic solvent and stirring it to get clear solution;
   b. followed by adding suitable premixing agent to the solution obtained in step (a) and further stirring to get a clear solution;
   c. further adding another premixing agent to the solution obtained in step (c) and mixing thoroughly to get a uniform dispersion;
   d. followed by addition of Lactose monohydrate and organic solvent to the solution obtained in step (c);
   e. thereafter the reaction mass obtained in step (d) was dried in a suitable drier; and
   f. the dried mass obtained in step (e) was sieved and further subjected to vacuum drying to obtain the Eliglustat premix.

The Eliglustat used in the step (a) is selected from crystalline form (s) or amorphous forms of Eliglustat free base of pharmaceutical acceptable salt thereof.

The organic solvent employed in step (a) is selected from halogenated hydrocarbons such as dichloromethane, 1,2-dichloroethane, chloroform and carbon tetrachloride; alcohols such as methanol, ethanol, isopropyl alcohol, 1-propanol, 2-propanol, 1-butanol, 2-butanol, and t-butyl alcohol; ketones such as acetone, ethyl methyl ketone, diethyl ketone, and methyl isobutyl ketone; esters such as ethyl acetate, n-propyl acetate, n-butyl acetate and t-butyl acetate; ethers such as diethyl ether, dimethyl ether, diisopropyl ether, methyl t-butyl ether and 1,4-dioxane; nitriles such as acetonitrile and propionitrile; water and mixtures thereof.

In one preferred embodiment the organic solvent employed in step (a) is selected from alcohols such as methanol, ethanol, isopropyl alcohol, 1-propanol, 1-butanol and t-butyl alcohol.

The premixing agent employed in step (b) and (c) are pharmaceutical excipients selected from the group comprising of polyvinylpyrrolidone (also called povidone), copovidone, polyvinyl alcohol, polyethylene glycol, polyol(Lactose, Mannitol), sodium starch glycolate, colloidal silicon dioxide (aerosil), hydroxypropyl cellulose, hydroxypropyl methylcellulose, methyl cellulose, carboxymethyl cellulose, sodium carboxymethyl cellulose, hydroxyethylcellulose, polyvinyl acetate, cyclodextrins, gelatins, hypromellose phthalate, sugars, silicates such as magnesium aluminometasilicate and combinations comprising one or more of the foregoing agents, Preferably selected from copovidone, lactose, magnesium aluminometasilicate, polyethylene glycol (PEG) and aerosol 200.

The drying step (e) and (f) may involve any of the prior art known solvent removal or drying techniques, wherein the drying of the Eliglustat premix means substantial removal of the solvent from the final Eliglustat premix, preferably greater than 90% solvent removal, more preferably 100% or complete solvent removal.

In another embodiment, the present invention provides a pharmaceutical composition comprising stable amorphous Eliglustat premix with pharmaceutically acceptable excipients.

The premix can be formulated into various pharmaceutical compositions like powder, granules, capsules, tablets, pellets etc.

In another embodiment, the present invention provides pharmaceutical compositions of Eliglustat or its pharmaceutically acceptable salts thereof in the form of mouth dissolving or sublingual tablet dosage form.

In another preferred embodiment, the present invention provides pharmaceutical compositions comprising the stable amorphous Eliglustat premix with pharmaceutically acceptable excipients wherein the total impurity in the finished product is not more than 3.0%, at accelerated stability condition of 40° C./75% RH or 30° C./75% RH or 30° C./65% RH or 25° C./60% RH, for duration such as 3, 6 or 12 months.

In another preferred embodiment, the present invention provides pharmaceutical compositions comprising the stable amorphous Eliglustat premix with pharmaceutically acceptable excipients wherein the total impurity in the finished product is not more than 2.5%.

In yet another preferred embodiment, the present invention provides pharmaceutical compositions comprising the stable amorphous Eliglustat premix with pharmaceutically acceptable excipients wherein the maximum unknown impurity in the finished product is not more than 0.2%, at accelerated stability condition of 40° C./75% RH or 30° C./75% RH or 30° C./65% RH or 25° C./60% RH, for duration such as 3, 6 or 12 months.

In another preferred embodiment, the present invention provides pharmaceutical compositions comprising the stable amorphous Eliglustat premix with pharmaceutically acceptable excipients wherein the N-oxide impurity in the finished product is not more than 2.0%, at accelerated stability condition of 40° C./75% RH or 30° C./75% RH or 30° C./65% RH or 25° C./60% RH, for duration such as 3, 6 or 12 months.

In an embodiment, the present invention provides sublingual tablets of Eliglustat wherein Eliglustat present in the dosage form is in the range of 10 mg to 200 mg or 20 mg to 100 mg or 25 mg to 50 mg as Eliglustat or its pharmaceutically acceptable salts thereof.

The pharmaceutical composition of the invention can be formed by various methods known in the art such as by dry granulation, wet granulation, melt granulation, direct blending & filling/compression, double compression, extrusion spheronization, layering and the like. The composition or formulation may be coated or uncoated. Coating of compositions such as tablets and caplets is well known in the art.

Pharmaceutically acceptable excipients may be utilized as required for conversion of the premixes into the final pharmaceutical dosage forms and include, for example, any one or more of diluents, binders, stabilizers, lubricants, glidants, disintegrating agents, surfactants, sweeteners, taste modifying agents, flavoring agents and other additives that are commonly used in solid pharmaceutical dosage form preparations.

Diluents:

Various useful fillers or diluents include but are not limited to starches, lactose, mannitol, cellulose derivatives, confectioner's sugar and the like. Different grades of lactose include but are not limited to lactose monohydrate, lactose DT (direct tableting), lactose anhydrous, Flowlac™, Pharmatose™ and others. Different starches include but are not limited to maize starch, potato starch, rice starch, wheat starch, pregelatinized starch and starch 1500, starch 1500 LM grade (low moisture content grade) from Colorcon, fully pregelatinized starch and others. Different cellulose compounds that can be used include crystalline celluloses and powdered celluloses. Examples of crystalline cellulose products include but are not limited to CEOLUS™ KG801, Avicel™ PH101, PH102, PH301, PH302 and PH-F20, PH112 microcrystalline cellulose 114, and microcrystalline cellulose 112. Other useful diluents include but are not limited to carmellose, sugar alcohols such as mannitol (Pearlitol™ SD200), sorbitol and xylitol, calcium carbonate, magnesium carbonate, dibasic calcium phosphate, and tribasic calcium phosphate.

Binders:

Various useful binders include but are not limited to hydroxypropyl celluloses, also called HPC (Klucel™ LF, Klucel EXF) and useful in various grades, hydroxypropylmethylcelluloses, also called hypromelloses or HPMC (Methocel™) and useful in various grades, polyvinylpyrrolidones or povidones (such as grades PVP-K25, PVP-K29, PVP-K30, and PVP-K90), Plasdone™ S-630 (copovidone), powdered acacia, gelatin, guar gum, carbomers (Carbopol™), methylcelluloses, polymethacrylates, and starches.

Disintegrants:

Various useful disintegrants include but are not limited to carmellose calcium, carboxymethylstarch sodium, croscarmellose sodium, crospovidones, examples of commercially available crospovidone products including but not limited to crosslinked povidone, Kollidon™ CL, Polyplasdone™ XL, XI-10, and INF-10 and low-substituted hydroxypropylcelluloses. Examples of low-substituted hydroxypropylcelluloses include but are not limited to low-substituted hydroxypropylcellulose LH11, LH21, LH31, LH22, LH32, LH20, LH30, LH32 and LH33. Other useful disintegrants include sodium starch glycolate, colloidal silicon dioxide, and starches.

Stabilizers:

Various useful stabilizers include basic inorganic salts, such as but not limited to basic inorganic salts of sodium, potassium, magnesium and calcium. Examples of basic inorganic salts of sodium are sodium carbonate, sodium hydrogen carbonate, sodium hydroxide, and the like. Examples of basic inorganic salts of potassium are potassium carbonate, potassium hydrogen carbonate, potassium hydroxide, and the like. Examples of basic inorganic salts of magnesium are heavy magnesium carbonate, magnesium carbonate, magnesium oxide, magnesium hydroxide, magnesium metasilicate aluminate, magnesium silicate, magnesium aluminate, synthetic hydrotalcite [$Mg_6Al_2(OH)_{16} \cdot CO3.4H2O$], aluminum hydroxide-magnesium [$2.5MgO \cdot Al_2O_3 \cdot xH_2O$], and the like. Examples of basic inorganic salts of calcium include precipitated calcium carbonate, calcium hydroxide, and the like.

Physical Form Stabilizers:

Various useful physical form stabilizers include various polymers such as but not limited to povidones like povidone k25, k30, k90 and the like, cellulose derivatives such as but not limited to hydroxypropyl cellulose, hydroxypropyl methyl cellulose, hydroxypropyl methyl cellulose acetyl succinate; silicate derivatives such as but not limited to colloidal silicon dioxide, magnesium alumino meta silicate and the like.

Surface-Active Agents:

Useful surface-active agents include non-ionic, cationic and anionic surface-active agents. Useful non-ionic surface-active agents include ethylene glycol stearates, propylene glycol stearates, diethylene glycol stearates, glycerol stearates, sorbitan esters (SPAN') and polyhydroxyethylenically treated sorbitan esters (TWEEN™), aliphatic alcohols and PEG ethers, phenol and PEG ethers. Useful cationic surface-active agents include quaternary ammonium salts (e.g. cetyltrimethylammonium bromide) and amine salts (e.g. octadecylamine hydrochloride). Useful anionic surface-active agents include sodium stearate, potassium stearate, ammonium stearate, and calcium stearate, triethenolamine stearate, sodium lauryl sulphate, sodium dioctylsulphosuccinate, and sodium dodecylbenzenesulphonate. Natural surface-active agents may also be used, such as for example phospholipids, e.g. diacylphosphatidylglycerols, diaceylphosphatidylcholines, and diaceylphosphatidic acids, the precursors and derivatives thereof, such as for example soybean lecithin and egg yolk.

Lubricants:

An effective amount of any pharmaceutically acceptable tableting lubricant can be added to assist with compressing tablets. Useful tablet lubricants include magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid and combinations thereof.

Glidants:

One or more glidant materials, which improve the flow of powder blends and minimize dosage form weight variation can be used. Useful glidants include but are not limited to silicon dioxide, talc and combinations thereof.

Coloring Agents:

Coloring agents can be used to color code the compositions, for example, to indicate the type and dosage of the therapeutic agent therein. Suitable coloring agents include, without limitation, natural and/or artificial compounds such as FD&C coloring agents, natural juice concentrates, pigments such as titanium oxide, silicon dioxide, iron oxides, zinc oxide, combinations thereof, and the like.

Flavoring Agents

The flavoring agents may comprise one or more synthetic or natural flavouring or aromatizing agents. Flavoring agents may be selected from essential oils including distillations, solvent extractions, or cold expressions of chopped flowers, leaves, peel or pulped whole fruit comprising mixtures of alcohols, esters, aldehydes and lactones; essences including either diluted solutions of essential oils, or mixtures of synthetic chemicals blended to match the natural flavour of the fruit, e.g., strawberry, raspberry and black currant; artificial and natural flavours of brews and liquors, e.g., cognac, whisky, rum, gin, sherry, port, and wine; tobacco, coffee, tea, cocoa, and mint; fruit juices including expelled juice from washed, scrubbed fruits such as lemon, orange, and lime; spear mint, pepper mint, wintergreen, cinnamon, cacoe/cocoa, vanilla, liquorice, menthol, eucalyptus, aniseeds, nuts (e.g., peanuts, coconuts, hazelnuts, chestnuts, walnuts, colanuts), almonds, raisins; and powder, flour, or vegetable material parts including tobacco plant parts, e.g., genus *Nicotiana*, in amounts not contributing significantly to the level of nicotine, and ginger.

Sweetening Agents

Sweetening agents are added essentially to improve the taste, and comprise one or more synthetic or natural sugars, i.e., any form of carbohydrates suitable for use as sweetener, as well as so called artificial sweeteners such as saccarin, sodium saccarin, aspartame, e.g., NutraSweet®, acesulfame K or acesulfame, potassium acesulfame, thaumatin, glycyrrhizin, sucralose, dihydrochalcone, alitame, miraculin, monellin, stevside.

Useful additives for coatings include but are not limited to plasticizers, antiadherents, opacifiers, solvents, and optionally colorants, lubricants, pigments, antifoam agents, and polishing agents.

Various useful plasticizers include but are not limited to substances such as castor oil, diacetylated monoglycerides, dibutylsebacate, diethyl phthalate, glycerin, polyethylene glycol, propylene glycol, triacetin, and triethyl citrate. Also, mixtures of plasticizers may be utilized. The type of plasticizer depends upon the type of coating agent. An opacifier like titanium dioxide may also be present, typically in an amount ranging from about 10% to about 20% based on the total weight of the coating.

The present invention includes administration of an effective amount of stable amorphous Eliglustat premix (either alone or as the active component of a pharmaceutical composition) for treatment of adult patients with Gaucher disease type 1 who are CYP2D6 extensive metabolizers (EMs), intermediate metabolizers (IMs), or poor metabolizers (PMs) as detected by an FDA-cleared test.

Detailed embodiments of the present invention are disclosed herein with the help of examples; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide and understandable description of the invention.

In particular, the processing conditions are merely exemplary and can be readily varied by one of ordinary skill in the art.

EXAMPLES

Example 1: Preparation of Amorphous Eliglustat Premix

| Ingredients | % w/w |
|---|---|
| Eliglustat | 37.9 |
| Hydroxypropyl methylcellulose | 19.1 |
| Tartaric acid | 7.0 |
| Lactose monohydrate | 10.7 |
| Magnesium aluminium silicate | 25.3 |

Brief Manufacturing Process
1. Eliglustat and tartaric acid were suspended in 40 ml of methanol and stirred to get clear solution;
2. Hydroxypropyl methylcellulose was added to the solution obtained in step (1) and further stirred to get a clear solution;
3. Magnesium aluminium silicate was added to the solution obtained in step (2) and mixed thoroughly to get a uniform dispersion;
4. Lactose monohydrate and 20 ml methanol were added to the solution obtained in step (3),
5. The reaction mass obtained in step (4) was dried in a rotavacuum drier;
6. The dried mass obtained in step (5) was sieved and further subjected to vacuum drying to obtain Eliglustat premix.

Example 2: Preparation of Amorphous Eliglustat Premix

| Ingredients | % w/w |
|---|---|
| Eliglustat | 37.9 |
| Copovidone | 9.49 |
| Tartaric acid | 7.0 |
| Lactose monohydrate | 45.5 |

Brief Manufacturing Process
i. Eliglustat and tartaric acid were suspended in 40 ml of methanol and stirred to get clear solution;
ii. Copovidone was added to the solution obtained in step (1) and further stirred to get a clear solution;
iii. Lactose monohydrate and 20 ml methanol were added to the solution obtained in step (2);
iv. The reaction mass obtained in step (3) was dried in a rotavacuum drier;
v. The dried mass obtained in step (4) was sieved and further subjected to vacuum drying to obtain Eliglustat premix.

Example 3: Preparation of Eliglustat Sublingual Tablets

| Ingredients | % w/w |
|---|---|
| Eliglustat hemitartrate | 25.0 |
| Mannitol | 43.0 |
| Microcrystalline Cellulose | 18.0 |
| Polyplasdone | 10.0 |
| Cheery Flavour | 0.5 |

-continued

| Ingredients | % w/w |
| --- | --- |
| Aspartame | 2.0 |
| Magnesium Stearate | 1.5 |

Brief Manufacturing Process
1. Eliglustat, Mannitol, Microcrystalline cellulose, Polyplasdone, Cheery flavour and Aspartame were sifted through a #40 mesh; and were mixed for 100 rotations;
2. Magnesium stearate was sifted through a #60 mesh and mixed with the blend obtained in step (1) for 25 rotations;
3. The blend obtained in step (2) was compressed into tablets by using rotary compression machine.

Example 4: Preparation of Eliglustat Sublingual Tablets

Example 4.1: Unit Formula

| Ingredients | % w/w |
| --- | --- |
| Eliglustat free base | 20.0 |
| Direct Compressible Mannitol | 39.0 |
| Direct Compressible Xylitol | 38.0 |
| Sucralose | 1.0 |
| Peppermint Flavour | 0.50 |
| Cooling Flavour | 0.50 |
| Magnesium Stearate | 1.00 |
| API Premix Weight | 100 |

Example 4.2: Unit Formula

| Ingredients | % w/w |
| --- | --- |
| Eliglustat free base | 20.0 |
| Direct Compressible Xylitol | 76.0 |
| Taste Masker | 1.0 |
| Sucralose | 1.0 |
| Peppermint Flavour | 0.50 |
| Cooling Flavour | 0.50 |
| Magnesium Stearate | 1.00 |
| API Premix Weight | 100 |

Example 4.3: Unit Formula

| Ingredients | % w/w |
| --- | --- |
| Eliglustat free base | 20.0 |
| Direct Compressible Xylitol | 56.0 |
| Amberlite resin | 38.0 |
| Sucralose | 1.0 |
| Peppermint Flavour | 0.50 |
| Cooling Flavour | 0.50 |
| Magnesium Stearate | 1.00 |
| API Premix Weight | 100 |

Brief Manufacturing Process for Sublingual Tablets:
1. Eliglustat, Mannitol, Xylitol, Sucralose & flavour where shifted through #30 mesh;
2. Blending the above materials from step 1) for 30 minutes in a blended at 20 RPM;
3. Followed by shifting magnesium stearate through #60 meshes and adding the shifted magnesium stearate to the blender of step 2) followed by blending for 5 minutes.
4. The final blend after step 3) was then compressed into tablets by using 6 mm punches.

Example 5: Preparation of Amorphous Eliglustat Tartrate Premix Unit Formula

| Ingredients | % w/w |
| --- | --- |
| Eliglustat | 37.9 |
| Tartaric acid | 7.0 |
| Lactose | 26.5 |
| Copovidone | 9.5 |
| Magnesium aluminometasilicate | 18.9 |

The total API premix weight in the unit is 222.3 mg.
Procedure for Preparing Eliglustat Premix:
1. Eliglustat and tartaric acid were dissolved in 60 ml of methanol in a buchi;
2. Copovidone was added into the solution obtained in step (1) and shaken well to get it dissolved completely;
3. Then Magnesium aluminometasilicate was added into the solution of step (2) and shaken well to get it uniformly dispersed;
4. Then Lactose was added into the step (3) resultant solution and shaken well to get it uniformly dispersed;
5. Then the reaction mass obtained in step (4) was dried in a rotavapor and the drying was continued at a temperature of 45° C. to remove the solvent;
6. Then the dried mass obtained in step (5) was collected and the collected Eliglustat Premix material was thereafter passed through 40 # and stored at 2-8° C. temperature.

Example 6: Preparation of Amorphous Eliglustat Tartrate Premix Unit Formula

| Ingredients | % w/w |
| --- | --- |
| Eliglustat | 37.9 |
| Tartaric acid | 7.0 |
| Lactose | 7.6 |
| Copovidone | 9.5 |
| Magnesium aluminometasilicate | 37.9 |

The total API premix weight in the unit is 222.3 mg.
Procedure for Preparing Eliglustat Premix:
1. Eliglustat and tartaric acid were dissolved in 60 ml of methanol in a buchi;
2. Copovidone was added into the solution obtained in step (1) and shaken well to get it dissolved completely;
3. Then Magnesium aluminometasilicate was added into the solution of step (2) and shaken well to get it uniformly dispersed;
4. Then Lactose was added into the step (3) resultant solution and shaken well to get it uniformly dispersed;
5. Then the reaction mass obtained in step (4) was dried in a rotavapor and the drying was continued at a temperature of 45° C. to remove the solvent;

6. Then the dried mass obtained in step (5) was collected and the collected Eliglustat Premix material was thereafter passed through 40 # and stored at 2-8° C. temperature.

Example 7: Preparation of Amorphous Eliglustat Tartrate Premix Unit Formula

| Ingredients | % w/w |
| --- | --- |
| Eliglustat | 37.9 |
| Tartaric acid | 7.0 |
| Lactose | 10.7 |
| Copovidone | 18.9 |
| Magnesium aluminometasilicate | 25.3 |

The total API premix weight in the unit is 222.3 mg.

Procedure for Preparing Eliglustat Premix:
1. Eliglustat and tartaric acid were dissolved in 60 ml of methanol in a buchi;
2. Copovidone was added into the solution obtained in step (1) and shaken well to get it dissolved completely;
3. Then Magnesium aluminometasilicate was added into the solution of step (2) and shaken well to get it uniformly dispersed;
4. Then Lactose was added into the step (3) resultant solution and shaken well to get it uniformly dispersed;
5. Then the reaction mass obtained in step (4) was dried in a rotavapor and the drying was continued at a temperature of 45° C. to remove the solvent;
6. Then the dried mass obtained in step (5) was collected and the collected Eliglustat Premix material was thereafter passed through 40 # and stored at 2-8° C. temperature.

Example 8: Preparation of Eliglustat Capsule

Unit Formula

| Ingredients | mg/capsule |
| --- | --- |
| Eliglustat Premix | 222.3 |
| Tartaric acid | 45.0 |
| Magnesium aluminometasilicate | 2.7 |

Brief Manufacturing Process:
1. Sifting of raw materials:
   Eliglustat Tartrate (premix) from any of the examples 1, 2, 5, 6, and 7; and microcrystalline cellulose were co-sifted through ASTM sieve #30 and collected into double polyethylene lined suitable container affixed with dully filled status label.
2. Blending:
   The above collected material from the sifting stage is then loaded into the blender and blended at 7 RPM for 30 minutes.
3. Lubrication:
   a. Glyceryl dibehenate was shifted through ASTM sieve #60;
   b. Then the blended material from the blending stage is unloaded and co-sifted with the sifted material from above step (a) through ASTM sieve #30;
   c. Then the sifted material from step (b) is loaded into bin blender and blended at 7 RPM for 10 minutes; and
   d. The blended material from step (c) is then unloaded and collected into double polyethylene lined suitable container affixed with dully filled status label.

It will be apparent to those skilled in the art that various modifications and variations can be made in the methods and compositions of the present inventions without departing from the spirit or scope of the invention. Thus, it is intended that the present invention cover the modification and variations of the invention provided they come within the scope of the appended claims and their equivalents.

Example 9: Dissolution of Eliglustat Capsule

The Eliglustat capsule prepared in Example 7 is then evaluated in various dissolution medium for release profile of the drug as shown in Table-1. The dissolution parameters are as follows:

A. Medium used for dissolution test of the capsule:
   i. Purified water,
   ii. 0.1 N Hydrochloric acid,
   iii. pH 3.0 citrate buffer,
   iv. pH 4.5 phosphate buffer, and
   v. pH 6.8 phosphate buffer.
B. Apparatus used: USP II apparatus.
C. RPM: 75 RPM.
D. Media Volume: 900 mL.
E. Time Points for sample collection (in minutes): 5, 10, 15, 20, 30, 45.

TABLE 1

Dissolution profile of the Eliglustat Capsule

| Media Time (min) | Purified water | 0.1N HCl | pH 3.0 citrate buffer | 4.5 pH Phosphate Buffer | 6.8 pH Phosphate Buffer |
| --- | --- | --- | --- | --- | --- |
| | Mean (% Drug release) | | | | |
| 0 | 0 | 0 | 0 | 0 | 0 |
| 5 | 59 | 68 | 66 | 58 | 53 |
| 10 | 75 | 83 | 79 | 78 | 77 |
| 15 | 80 | 91 | 82 | 84 | 84 |
| 20 | 83 | 93 | 84 | 88 | 86 |
| 30 | 87 | 95 | 87 | 90 | 88 |
| 45 | 89 | 96 | 90 | 91 | 90 |

Example 10: A Comparative Experimental Trial Done to Evaluate the Eliglustat Normal Mixture Vs Eliglustat Premix for Consistency A. Preparation of Eliglustat Mixture:
1. Eliglustat free base and tartaric acid were dissolved in suitable organic solvent like methanol, followed by drying the solvent by suitable evaporation techniques like rota-evaporation, etc., to give sample A-1.
2. Eliglustat crystalline for and tartaric acid were dissolved in suitable organic solvent like methanol, followed by drying the solvent by suitable evaporation techniques like rota-evaporation, etc., to give sample A-2.

B. Preparation of Eliglustat Premix:

The Eliglustat premix can be prepared using the method used in any of the above stated Example 1-7. For instance in the comparative example Eliglustat premix was prepared by using the procedure as in Example 2, wherein:
  i. Eliglustat and tartaric acid were suspended in 40 ml of methanol and stirred to get clear solution;
  ii. Copovidone was added to the solution obtained in step (1) and further stirred to get a clear solution;
  iii. Lactose monohydrate and 20 ml methanol were added to the solution obtained in step (2);
  iv. The reaction mass obtained in step (3) was dried in a rotavacuum drier;
  v. The dried mass obtained in step (4) was sieved and further subjected to vacuum drying to obtain Eliglustat premix, as Sample B-1.

Observation:

| Sample Name | Solvent | Active | Additive | Premixing Agent | Remarks |
| --- | --- | --- | --- | --- | --- |
| A-1 | Methanol | Eliglustat free base | Tartaric Acid | Not present | Gummy mass observed |
| A-2 | Methanol | Crystalline Eliglustat Tartarate | — | Not present | Gummy mass observed |
| B-1 | Methanol | Eliglustat free base | Tartaric acid | Copovidone/Lactose Monohydrate or both | Free flowing physically stable premix obtained |
| B-2 | Methanol | Crystalline Eliglustat Tartarate | — | Copovidone/Lactose Monohydrate or both | Free flowing physically stable premix obtained |

Form the above table it is clear that final yield of amorphous form of eliglustat tartarate prepared either from eliglustat tartarate crystalline form or eliglustat and tartaric acid is gummy in nature and is not suitable for further processing or for the formulation development. However the Eliglustat premix as prepared in the present invention leads to a stable free flowing Eliglustat premix, which can be used to prepare a stable pharmaceutical formulation like sublingual table or capsule which is more stable than any other Eliglustat forms.

Stability Studies of the Eliglustat Capsule

The Eliglustat Premix containing capsules of the present invention were evaluated initially and also under accelerated stability conditions for formation of total impurities. The stability data of the capsule were found to be satisfactory due to the stability attribute of the amorphous Eliglustat premix which is itself of better stability. The stability results of capsule composition are shown in Table-2 & Table-3.

TABLE 2

Test Condition for Eliglustat Capsule, in Blister Pack

| Impurities | RT/INITIAL | 25° C./60% RH_3 M | 30° C./75% RH_3 M | 40° C./75% RH_3 M |
| --- | --- | --- | --- | --- |
| N-oxide Impurity (NMT 2.5%) | 0.062% | 0.191% | 0.326% | 0.722% |
| Max. Unknown (NMT 0.2%) | 0.041% | 0.040% | 0.040% | 0.049% |
| Total Impurities (NMT 3.5%) | 0.10% | 0.23% | 0.40% | 0.92% |

TABLE 3

Test Condition for Eliglustat Capsule, in HDPE Bottle Packing

| Impurities | RT/INITIAL | 25° C./60% RH_3 M | 30° C./75% RH_3 M | 40° C./75% RH_3 M |
| --- | --- | --- | --- | --- |
| N-oxide Impurity (NMT 2.5%) | 0.062% | 0.207% | 0.348% | 0.781% |
| Max. Unknown (NMT 0.2%) | 0.041% | 0.037% | 0.041% | 0.043% |
| Total Impurities (NMT 3.5%) | 0.10% | 0.24% | 0.42% | 0.89% |

The stability data provided in the above tables 2 & 3, clearly indicated that the proposed Eliglustat premix based composition is more stable and within the threshold limits of impurities and the stability of the composition is to be attributed to the stability of the premix itself.

Further stability data is provided for the composition at higher stress condition of 40° C./75% RH for a period of 1-3 months as shown in below Table-4 & 5:

TABLE 4

Test Condition for Eliglustat Capsule: 40° C./75% in Blister Pack

| Impurities | RT/INITIAL | 40° C./75% RH_1 M | 40° C./75% RH_2 M | 40° C./75% RH_3 M |
| --- | --- | --- | --- | --- |
| N-oxide Impurity (NMT 2.5%) | 0.062% | 0.242% | 0.479% | 0.722% |
| Max. Unknown (NMT 0.2%) | 0.041% | 0.041% | 0.038% | 0.049% |
| Total Impurities (NMT 3.5%) | 0.10% | 0.32% | 0.52% | 0.92% |

TABLE 5

Test Condition for Eliglustat Capsule: 40° C./75% in HDPE Bottle Packing (Under accelerated Stability) for periods of 1-3 months:

| Impurities | RT/INITIAL | 40° C./75% RH_1 M | 40° C./75% RH_2 M | 40° C./75% RH_3 M |
| --- | --- | --- | --- | --- |
| N-oxide Impurity (NMT 2.5%) | 0.062% | 0.243% | 0.526% | 0.781% |

TABLE 5-continued

Test Condition for Eliglustat Capsule: 40° C./75% in HDPE Bottle Packing (Under accelerated Stability) for periods of 1-3 months:

| Impurities | RT/INITIAL | 40° C./75% RH_1 M | 40° C./75% RH_2 M | 40° C./75% RH_3 M |
|---|---|---|---|---|
| Max. Unknown (NMT 0.2%) | 0.041% | 0.039% | 0.041% | 0.043% |
| Total Impurities (NMT 3.5%) | 0.10% | 0.32% | 0.57% | 0.89% |

The stability data provided in the above tables, clearly indicated that in the proposed Eliglustat premix based composition is found to be stable and within the threshold limits of impurities and the stability of the composition is to be attributed to the stability of the premix itself.

Figure 2:
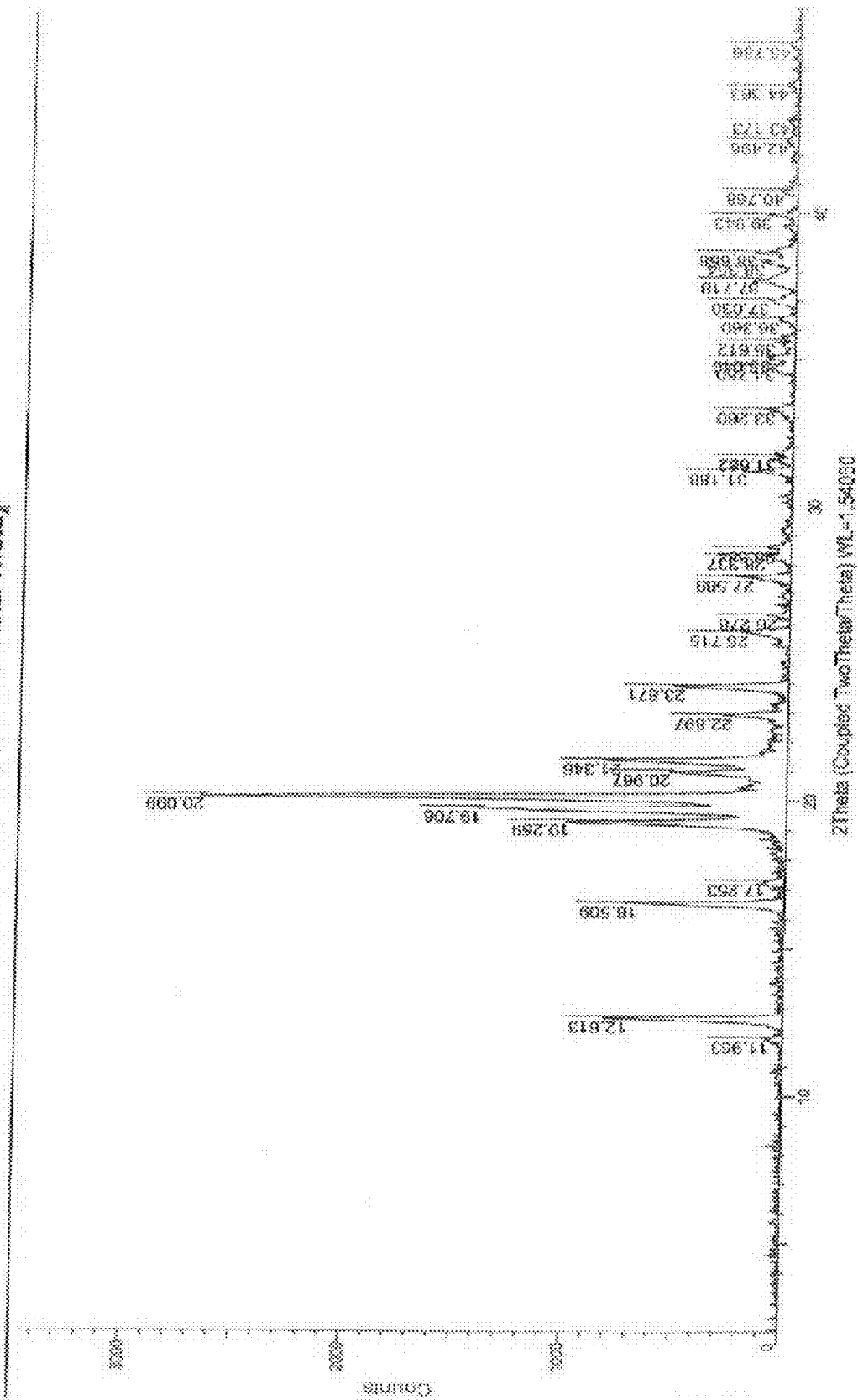
FIG. 2: PXRD pattern of Eliglustat Tartrate API.
Figure 3:
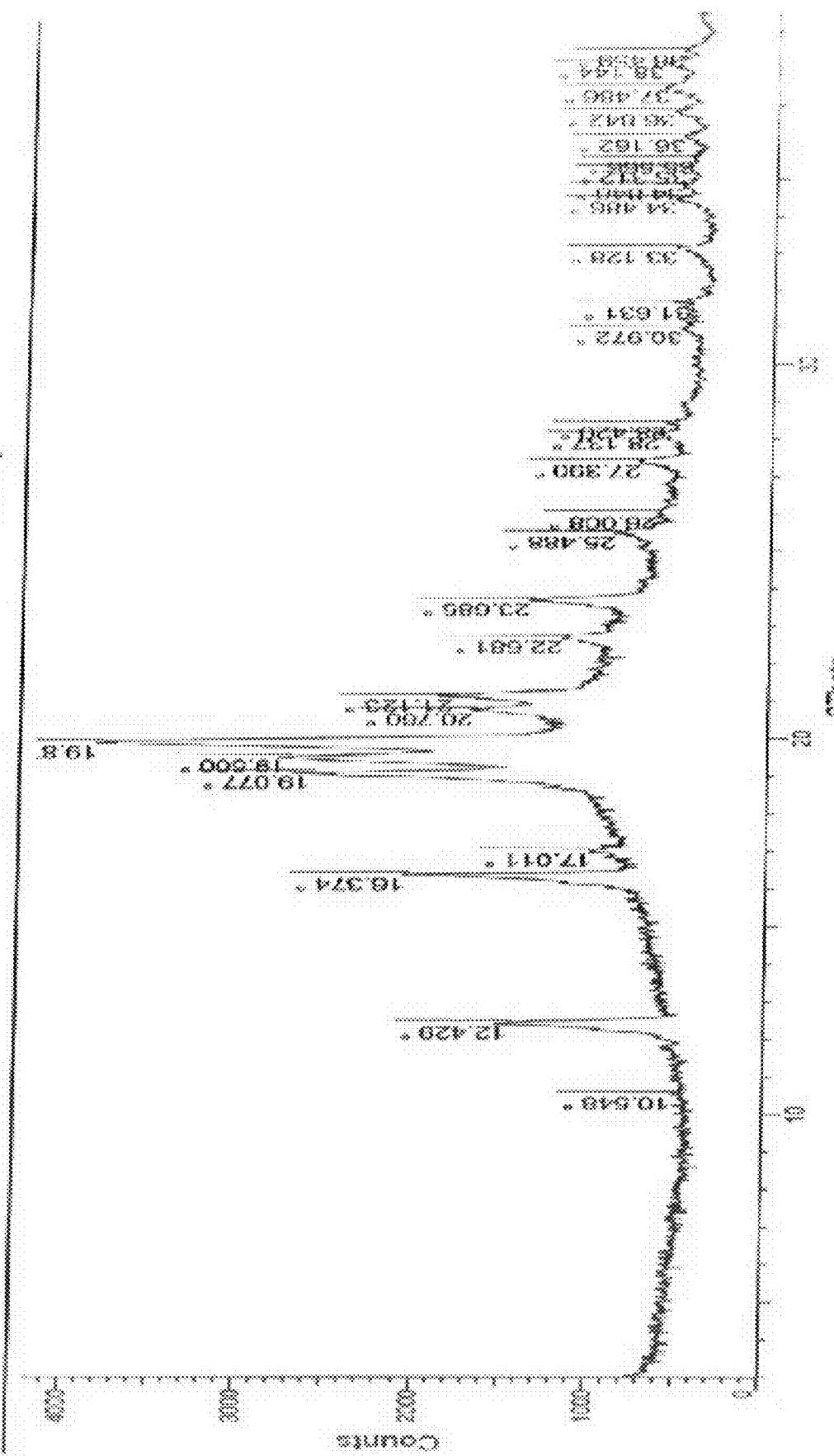
FIG. 3: PXRD pattern of Eliglustat Premix at 2-8° C. after 50 Days.
Figure 4:
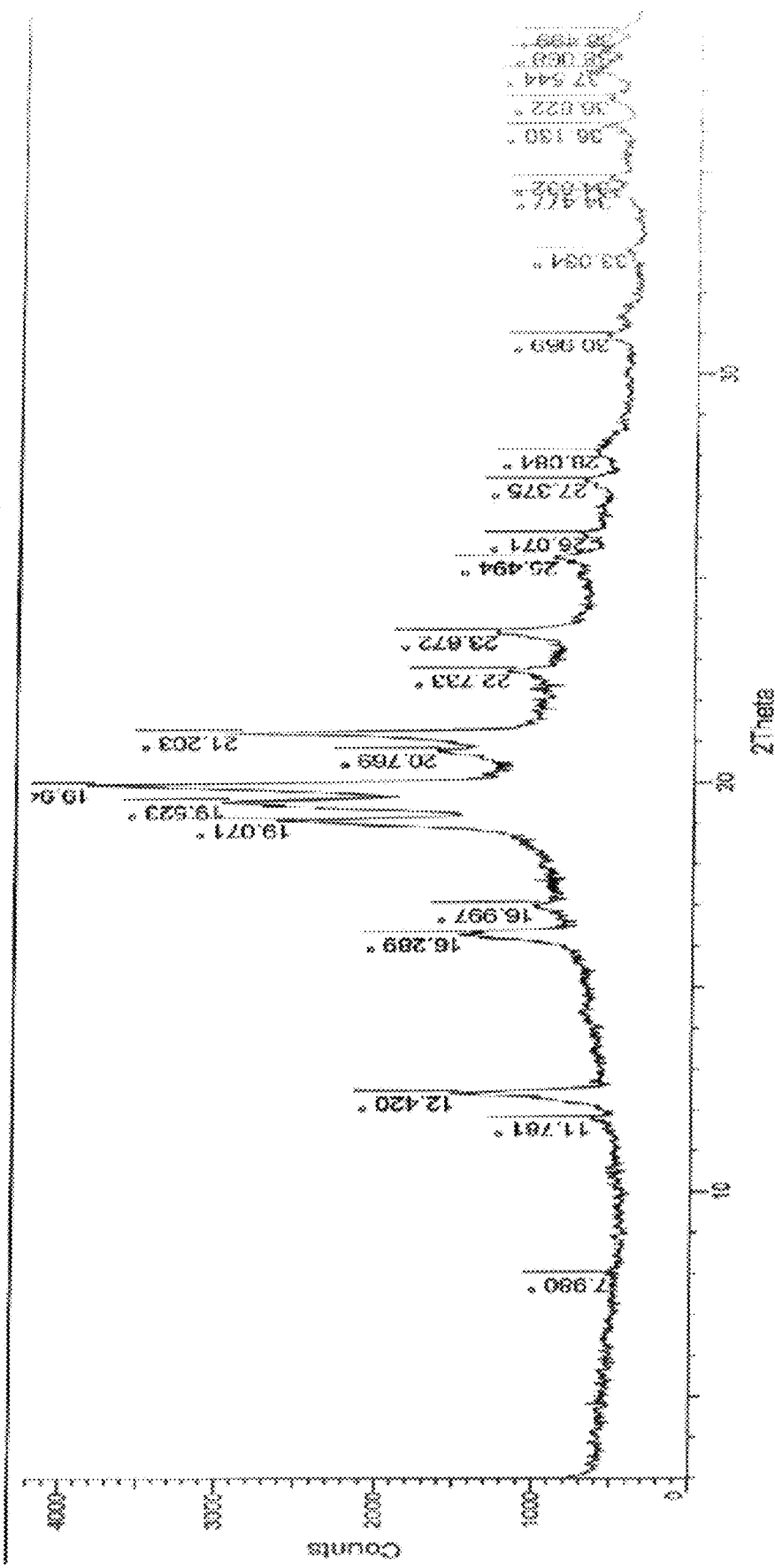
FIG. 4: PXRD pattern of Eliglustat Premix at Room Temperature after 50 Days.

Powder X-Ray Diffraction (PXRD) data for the Premix and composition were generated using Analytical Instrument and compared for better understanding as shown in FIGS. 1-4.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A stable pharmaceutical composition of amorphous Eliglustat which comprises:
   i. a stable amorphous Eliglustat premix comprising of Eliglustat or its pharmaceutically acceptable salt with at least one premixing agent, and
   ii. at least one stabilizer comprising basic inorganic salts of magnesium, and
   iii. optionally, at least one pharmaceutically acceptable excipient, wherein the said premix is free flowing.

2. The stable pharmaceutical composition as claimed in claim 1, wherein the at least one premixing agent is selected from diluents, lubricants, disintegrants, glidants, and surface active agents and mixture thereof.

3. The stable pharmaceutical composition as claimed in claim 1, wherein the at least one premixing agent is selected from the group consisting of polyvinylpyrrolidone, copovidone, polyvinyl alcohol, lactose, polyethylene glycol, polyol, sodium starch glycolate, colloidal silicon dioxide, hydroxypropyl cellulose, hydroxypropyl methylcellulose, methyl cellulose, carboxymethyl cellulose, sodium carboxymethyl cellulose, hydroxyethylcellulose, polyvinyl acetate, cyclodextrins, gelatins, hypromellose phthalate, sugars, magnesium aluminometasilicate, fumed silica and combinations thereof.

4. The stable pharmaceutical composition as claimed in claim 1, wherein the amorphous Eliglustat premix is prepared by a process comprising of:
   a. dissolving a mixture of Eliglustat with suitable additive or excipient in an organic solvent and stirring it to get a clear solution;
   b. adding suitable premixing agent to the solution obtained in step (a) and further stirring to get a clear solution;
   c. adding second premixing agent and stabilizer to the solution obtained in step (b) and mixing thoroughly to get a uniform dispersion;
   d. adding organic solvent to the solution obtained in step (c);
   e. removing said organic solvent;
   f. drying the mass obtained in step (e);
   g. sieving the mass obtained in step (f); and
   h. vacuum drying the mass of step (g) for complete solvent removal to obtain the Eliglustat premix which is free flowing.

5. The stable pharmaceutical composition as claimed in claim 4, wherein the organic solvent in step (a) and (d) is selected from the group consisting of halogenated hydrocarbons selected from dichloromethane, 1,2-dichloroethane, chloroform and carbon tetrachloride; alcohols selected from methanol, ethanol, isopropyl alcohol, 1-propanol, 2-propanol, 1-butanol, 2-butanol, and t-butyl alcohol; ketones selected from acetone, ethyl methyl ketone, diethyl ketone, and methyl isobutyl ketone; esters selected from ethyl acetate, n-propyl acetate, n-butyl acetate and t-butyl acetate; ethers selected from diethyl ether, dimethyl ether, diisopropyl ether, methyl t-butyl ether and 1,4-dioxane; nitriles selected from acetonitrile and propionitrile and mixtures thereof.

6. The stable pharmaceutical composition as claimed in claim 4, wherein the organic solvent in step (a) and (d) is alcohol selected from the group consisting of methanol, ethanol, isopropyl alcohol, 1-propanol, 1-butanol and t-butyl alcohol.

7. The stable pharmaceutical composition as claimed in claim 1, wherein the composition is a solid dosage form selected from powder, granules, capsules, tablets, films, sublingual tablets or mouth dissolving tablets and pellets.

8. The stable pharmaceutical composition as claimed in claim 1, wherein a content of total impurities in the composition is not more than 3.0% under accelerated stability conditions for a storage period of 3, 6 or 12 months.

9. The stable pharmaceutical composition as claimed in claim 1, wherein a content of any unknown impurities in the composition is not more than 0.2% under accelerated stability conditions for a storage period of 3, 6 or 12 months.

10. The stable pharmaceutical composition as claimed in claim 1, wherein a content of N-oxide impurity in the composition is not more than 2.0% under accelerated stability conditions for a storage period of 3, 6 or 12 months.

11. The stable pharmaceutical composition of claim 1, wherein said basic inorganic salts of magnesium is heavy magnesium carbonate, magnesium carbonate, magnesium oxide, magnesium hydroxide, magnesium metasilicate aluminate, magnesium silicate, magnesium aluminate, synthetic hydrotalcite, or aluminum hydroxide-magnesium.

12. A stable sublingual tablet composition of amorphous Eliglustat which comprises:
   i. a stable amorphous Eliglustat premix comprising of Eliglustat or its pharmaceutically acceptable salt with at least one premixing agent, and
   ii. at least one stabilizer, and
   iii. optionally, at least one pharmaceutically acceptable excipient, wherein the said premix is free flowing.

* * * * *